United States Patent [19]

Hardtmann et al.

[11] 4,452,787
[45] Jun. 5, 1984

[54] 1-SUBSTITUTED TRICYCLIC QUINAZOLINONES HAVING BIOLOGICAL ACTIVITY AS TRANQUILIZERS

[75] Inventors: Goetz E. Hardtmann, Morristown; William J. Houlihan, Mt. Lakes, both of N.J.

[73] Assignee: Sandoz, Inc., E. Hanover, N.J.

[21] Appl. No.: 427,197

[22] Filed: Sep. 29, 1982

Related U.S. Application Data

[63] Continuation-in-part of Ser. No. 302,483, Sep. 16, 1981, abandoned.

[51] Int. Cl.$^3$ .................. A61K 31/505; C07D 487/04
[52] U.S. Cl. ...................................... 424/251; 544/250
[58] Field of Search ........................ 544/250; 424/251

[56] References Cited

U.S. PATENT DOCUMENTS

| 3,280,117 | 10/1966 | Griot | 544/250 X |
| 3,598,823 | 8/1971 | Hardtmann | 544/250 |
| 3,621,025 | 11/1971 | Jen et al. | 544/250 |
| 3,887,559 | 6/1975 | Hardtmann | 544/250 |
| 3,905,976 | 9/1975 | Hardtmann | 544/250 |
| 3,963,720 | 6/1976 | Hardtmann | 544/247 |

FOREIGN PATENT DOCUMENTS

2008998 9/1971 Fed. Rep. of Germany.

OTHER PUBLICATIONS

Hardtmann et al., J. Med. Chem., vol. 18(5), pp. 447–453 (1975).
Vlasenko et al., Chemical Abstracts, vol. 85, 123861u (1976).
Grout et al., J. Chem. Soc., (1960), pp. 3551–3557 (1960).

*Primary Examiner*—Donald G. Daus
*Assistant Examiner*—Diana G. Rivers
*Attorney, Agent, or Firm*—Gerald D. Sharkin; Richard E. Vila

[57] ABSTRACT

Tranquilizers are of the formula I:

wherein
R° is hydrogen, halo of atomic weight of from 18 to 80, i.e. fluoro, chloro or bromo, or alkyl of 1 to 3 carbon atoms,
R is hydrogen, halo of atomic weight of from 18 to 80, alkyl of 1 to 4 carbon atoms, nitro or trifluoromethyl,
n is 0 or 1,
$R_1$, $R_2$ and $R_3$ are each independently hydrogen or alkyl of 1 or 2 carbon atoms, with the proviso that no more than 2 of $R_1$, $R_2$ and $R_3$ are other than hydrogen,
Z is (a) $-(CH)_m$—phenyl with R′ and Y°, Y substituents;

(b) $-(CH_2)_q$—pyridyl;

(c) $O-(CH_2)_p$—phenyl with Y°, Y substituents; or (d) $-CH-CH-$ (with $CH_2$ bridge)—phenyl with Y°, Y substituents.

R′ is hydrogen or alkyl of 1 or 2 carbon atoms,
Y° is hydrogen, halo of atomic weight of from 18 to 80 or alkyl of 1 to 3 carbon atoms,
Y is hydrogen, halo of atomic weight of from 18 to 80, alkyl of 1 to 4 carbon atoms, trifluoromethyl or nitro,
p is 1 or 2,
q is 0, 1 or 2, and
m is 0, 1, 2, 3 or 4.

22 Claims, No Drawings

1-SUBSTITUTED TRICYCLIC QUINAZOLINONES HAVING BIOLOGICAL ACTIVITY AS TRANQUILIZERS

This is a continuation-in-part of application Ser. No. 302,483 filed Sept. 16, 1981 now abandoned.

The present invention relates to substituted tricyclic compounds which are quinazolinones, and also relates to methods and compositions for utilization of the compounds based on their biological activity as tranquilizers.

The compounds whose tranquilizer activity forms the basis for the present invention may be represented by the following structural formula I:

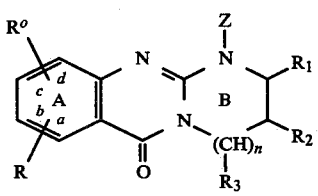

wherein
  $R^o$ is hydrogen, halo of atomic weight of from 18 to 80, i.e. fluoro, chloro or bromo, or alkyl of 1 to 3 carbon atoms,
  R is hydrogen, halo of atomic weight of from 18 to 80, alkyl of 1 to 4 carbon atoms, nitro or trifluoromethyl,
  n is 0 or 1,
  $R_1, R_2$ and $R_3$ are each independently hydrogen or alkyl of 1 or 2 carbon atoms, with the proviso that no more than 2 of $R_1$, $R_2$ and $R_3$ are other than hydrogen,
  Z is

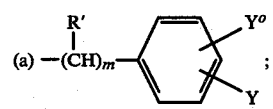

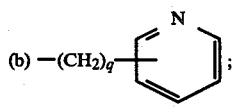

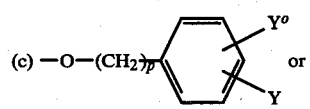

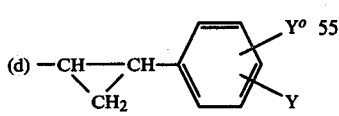

R' is hydrogen or alkyl of 1 or 2 carbon atoms,
  $Y^o$ is hydrogen, halo of atomic weight of from 18 to 80 or alkyl of 1 to 3 carbon atoms,
  Y is hydrogen, halo of atomic weight of from 18 to 80, alkyl of 1 to 4 carbon atoms, trifluoromethyl or nitro.
  p is 1 or 2,
  q is 0, 1 or 2, and
  m is 0, 1, 2, 3 or 4.

The compounds of the formula I in which R is other than hydrogen when n is 0 and Z is of type (a) are novel and also form are part of the present invention.

The compounds of the formula I may be prepared in a process (a) by reacting a compound of the formula II

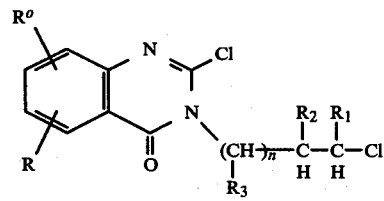

wherein $R^o$, R, $R_1$, $R_2$, $R_3$ and n are as above defined with a compound of the formula III:

$$Z-NH_2 \qquad \text{III}$$

wherein Z is as defined.

The preparation of the compounds of the formula I in process (a) by reaction of compounds II and III may be suitably carried out temperatures of from 20° C. to 160° C., preferably 40° C. to 90° C. The reaction is conveniently carried out in the presence of an inert organic solvent such as dimethylacetamide or a lower alkanol, e.g. ethanol. The resulting reaction product of the formula I may be recovered from the resulting reaction mixture by working up by established procedures.

The compounds of the formula I may also be prepared in a process (b) by reacting a compound of the formula IV:

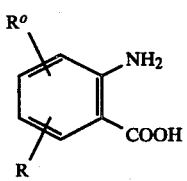

wherein $R^o$ and R are as defined, with a compound of the formula V:

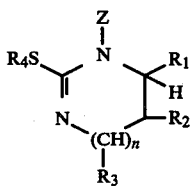

wherein $R_1$, $R_2$, $R_3$, n and Z are as defined and $R_4$ is alkyl of 1 to 4 carbon atoms or benzyl.

The preparation of compounds I in process (b) by the reaction of compounds IV and V may be suitably carried out at elevated temperatures typically in the range of from 100° C. to 190° C., preferably 140° C. to 180° C. The reaction is conveniently carried out in an inert organic solvent of conventional type, preferably a higher boiling organic solvent such as dimethylacetamide and dimethylformamide, more preferably dimethylacetamide. The reaction products of formula I may be recovered from the reaction mixture by working up by established procedures.

The compounds of the formula I may also be prepared in a process (c) by reacting a compound of the formula VI:

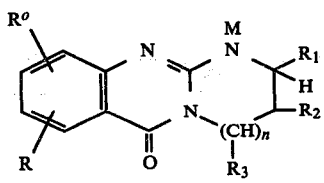

VI wherein $R^o$, R, $R_1$, $R_2$, $R_3$ and n are as defined and M is an alkali metal, with a compound of the formula VII:

X—Z    VII wherein Z is as defined and X is halo of atomic weight of from 35 to 130.

Process (c) is also of known type and may be effected as described in U.S. Pat. No. 3,598,823.

The compound of the formula I may further be prepared in a process (d) by reaction of a compound of the formula VIII:

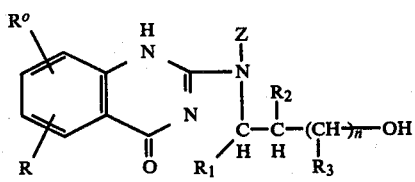

VIII wherein $R^o$, R, $R_1$, $R_2$, $R_3$, n and Z are as defined, with a cyclizing agent, and treating the reaction product with an acid binding agent.

Process (d) may be effected under the conditions described for the analogous reaction in U.S. Pat. Nos. 3,887,559 and 3,905,976.

The intermediary reactants of the formulae II, III, IV, V, VI, VII and VIII are either known per se or may be prepared from known materials in accordance with procedures described in the literature.

The compounds of the formula I form acid addition salts which are included within the scope of the present invention. Those salts forming pharmaceutically acceptable salt forms, e.g. the hydrochloride, may of course be used pharmaceutically in accordance with the invention. The acid addition salts may be produced from the corresponding free bases by conventional procedures. Conversely, the free bases may be obtained from the salts by procedures known in the art.

The compounds of the formula I exhibit a Central Nervous System depressant effect in mammals and are useful as tranquilizers as indicated by the Flunitrazepam Receptor Binding Assay in accordance with the method basically described by R. C. Speth et al., *Life Science*, 22:859 (1978), and by the conflict segment of the well known Geller Conflict test in rats (1–20 mg./kg.) as described by J. Geller, Psychopharmacologia, Vol. 1, pages 482–492 (1960).

Routine and non-substantive modifications of the Flunitrazepam Receptor Binding Assay (hereinafter FBA TEST No. 1) that are evident from the following description are employed in such evaluation in which non-radioactive candidate compounds are tested for their ability to displace $^3H$-flunitrazepam binding from isolated calf brain benzodiazepine receptors. Hence, an aliquot of frozen calf caudate tissue is thawed and diluted with 0.5 M Tris buffer containing metal ions (120 mM NaCl, 5 mM KCL, 2 mM $CaCl_2$ and 1 mM $MgCl_2$) to a final concentration of 8 mg/ml, i.e., a 25 fold dilution. This suspension is made homogenous by homogenation with a Brinkmann Polytron using a rheostat setting of 8 for 10 seconds. Ten $\lambda$ of $^3H$-flunitrazepam solution is diluted in 0.05 M Tris buffer (pH 7.1 at 37° C.) to give a concentration of 10 nM ($3.13 \times 10^{-6}$ mg/ml). This solution is stored frozen at $-20°$ C., while the stock $^3H$-flunitrazepam solution in ethanol is kept refrigerated at $+2°$ C. Periodically, the stock ethanolic $^3H$-flunitrazepam solution is examined by TLC for chemical purity. If the purity becomes <90%, the stock solution is repurified or new high purity $^3H$-flunitrazepam is obtained and the impure $^3H$-flunitrazepam discarded. A 0.1 ml portion of 10 mM $^3H$-flunitrazepam "working" solution is added to $12 \times 75$ mm borosilicate disposable test tube along with 0.1 ml of freshly prepared 10% ethanol solution. This is the control tube for measuring total binding. Non-specific binding is determined by the addition of $2 \times 10^{-5}$ M diazepam (in 10% ethanol) to other tubes in the place of 0.1 ml 10% ethanol. The specific binding is determined in the final results by subtraction of the non-specific binding from the total binding. All compounds screened have their results expressed in terms of specific binding and are tested at a final concentration of $1 \times 10^{-6}$ M. Three mg of each compound are placed in $18 \times 150$ mm borosilicate disposable test tubes. These tubes are kept in the dark at room temperature until the day of the assay at which time 10 ml of absolute ethanol is added and the tubes placed in a Branson Ultrasonic Cleaner for 15 minutes and then vortexed in order to put the compounds into solution. All tubes are closely examined to make certain the compound is completely in solution. If not, then 3 drops of 2 N HCl is added. If the compound is still not in solution but a cloudy homogenous suspension is found, then the subsequent serial dilutions are continued. This gives a concentration of $\sim 1 \times 10^{-3}$ M. The compounds are further diluted by serial dilution as follows: 0.1 ml of the $10^{-3}$ M solution is added to 0.9 ml of 100% ethanol and vortexed. A 0.1 ml portion of this solution is added to 0.9 ml of water to give $\sim 1 \times 10^{-5}$ M solution. A 0.1 ml portion of this solution is added to $12 \times 75$ mm test tubes for assay. All assays are run in duplicate. A 0.8 ml portion of caudate tissue suspension is added to all tubes, vortexed, incubated at 2° C. for 120 minutes, and rapidly filtered under vacuum through Whatman GF/G glass fiber filters. Each tube is rinsed once with 3 ml ice-cold 50 mM Tris buffer (pH 7.1 at 37° C.) and the filter subsequently washed once with 6 ml of the same Tris buffer. The $^3H$-flunitrazepam trapped on the filters is counted by liquid scintillation counting on a Beckman LS 8000 after the filters are rapidly shaken for 45 minutes in the scintillation vials with 10 ml of scintillation cocktail. Results of compounds screened are calculated by the on-line data reduction system in the Beckman LS 8000, and are expressed as a percent specifically bound compared to control.

Benzodiazepine receptors are obtained from male Holstein calves. Immediately after exsanguination, the brains are quickly removed and placed in ice. Dissection of the caudate nucleus is completed within 2 hours after sacrifice and the tissue weighed, and homogenized (1:10, W/V) in 0.05 M Tris buffer (pH 7.1 at 37° C.)

using a Brinkmann Polytron for 10 seconds with a rheostat setting of 8. The homogenate is centrifuged for 10 minutes at 20,000 RPM in a Sorvall RC2B centrifuge using a SS 34 head. The supernatant is decanted and the pellet washed twice to remove endogenous dopamine by resuspension with the use of the Brinkmann Polytron and recentrifugation. The final pellet is resuspended in 0.05 M Tris (pH 7.1 at 37° C.) containing 120 mM NaCl, 5 mM KCl, 2 mM $CaCl_2$, and 1 mM $MgCl_2$ in a final concentration of 200 mg wet weight starting material/ml of buffer. The homogenate is stored in 4 ml aliquots in glass bottles in liquid nitrogen.

Substantially similar results are obtainable in a Flunitrazepam Receptor Binding Assay as described by Chang et. al., Eur. J. Pharmacol., 48, 213 (1978): when carried out with the non-substantive modifications evident from the following description (hereinafter FBA TEST No. 2): Fresh calf brain cortex is homogenized in a 19 fold volume of Tris-HCl buffer pH 7.4, using a Brinkman Polytron PT 20 and centrifuged at 50'000 g for 10 min. The pellets are frozen at $-20°$ C. and resuspended in a 400 fold volume of Tris-buffer pH 7.4 before use for the binding assay. The assay mixtures consist of 1.8 ml of homogenate (corresponding to 4.5 mg of original tissue), 0.1 ml [$^3$H]-Flunitrazepam (final concentration 1.5 nM), and 0.1 ml of buffer for determination of total binding or 0.1 ml of unlabelled Flunitrazepam (final concentration 1 $\mu$M) for determination of nonspecific binding, respectively. To assess the potency of various drugs in inhibiting specific binding, drugs are added (instead of buffer) to give 5 to 9 different concentrations between 1 nM and 10 $\mu$M, each in duplicate. After incubation for 15 min at 0° C., the assay mixtures are rapidly filtered through Whatman GF/B filters and washed twice with 5 ml of ice cold Tris-buffer. The filters are counted in Rialuma on a LKB Rach-Beta Liquid Scintillation Counter. $IC_{50}$ values (concentration of a test drug which inhibits specific binding of $^3$H-Flunitrazepam by 50%) are determined by linear regression analysis (HILL-Plot).

In other evaluations of benzodiazepine receptors involving the rat brain it is observed that the compounds of the formula I interact in a mode which differs from that of benzodiazepine in two different specific assays as follows:

1. In a Flunitrazepam Receptor Binding Assay as described by Speth et al., above, the compounds of the formula I exhibit—in contrast to classical benzodiazepines—a higher affinity for benzodiazepine receptors in cerebellum compared to hippocampus suggesting a more potent interaction with type I benzodiazepine receptors than with type II benzodiazepine receptors.

2. The compounds of formula I exhibit a differential interaction with benzodiazepine receptors after photoaffinity labelling with flunitrazepam when examined by the method described in Neuroscience Letters, 31 (1982), pages 65-69. In this assay conventional benzodiazepines exhibit after photoaffinity labelling with flunitrazepam when compared to untreated membranes a 20-fold and more increased $IC_{50}$ values after photoaffinity labelling whereas benzodiazepine antagonists exhibit unaltered $IC_{50}$ values. The compounds of formula I exhibit only up to 4-fold increased $IC_{50}$ values after photoaffinity labelling of benzodiazepine receptors when compared to the values obtained with control membranes. In addition, compounds of formula I exhibit increased affinity for benzodiazepine receptors of rat cerebral cortex in presence of 4-aminobutyric acid when compared to their respective affinity in the absence of 4-aminobutyric acid.

The mode of interaction of the compound of the formula I with benzodiazepine receptors therefore differs from that of conventional benzodiazepines and from that of benzodiazepine antagonists. The compounds of formula I possess a relatively high level of activity in the above indicated tests and possess an interesting and desirable spectrum of tranquilizer activity, particularly anti-anxiety activity. In addition, the compounds of formula I are indicated to have a stimulating effect on behavior in observation tests and to lack undesirable CNS depressant effects. For example, the compounds of the formula I are also indicated to be active in the well known hexobarbital reinduction test. However, at the doses at which the compounds are indicated to be useful as minor tranquillizers, e.g. by the FBA test and the conflict segment of the Geller Conflict test, the compounds I are generally indicated to be only weakly active or essentially inactive in a number of other standard CNS depressant tests, such as in sleep studies in monkeys, spinal reflex test in cats, the chemically induced convulsions test (in mice with N-sulfamoyl hexahydrol azepine), the Dunham rotarod test and, of further interest, in the variable interval segment of the Geller Conflict test. The compounds I are therefore indicated to have a very specific and desirable mode of action in effecting tranquillization, and in particular are indicated to effect tranquillization with a substantially reduced sedative action which is associated with, e.g. drowsiness, in most if not all of the currently available tranquilizers.

For such use as tranquilizers, more particularly in the treatment of anxiety and/or tension, the amount of the compound of the formula I to be administered will vary depending upon the compound used, mode of administration, the condition being treated, the severity of the condition and other known factors. However, in general satisfactory results are obtained when administered at a daily dosage of from 0.1 to 100 milligrams per kilogram of body weight, preferably given orally and in divided doses 2 to 4 times a day, or in sustained release form. For larger mammals the administration of from 10 to 500 milligrams per day provides satisfactory results and dosage forms for internal administration comprise from 2.5 to 250 milligrams of the compound in admixture with a solid or liquid carrier. The daily dosage for larger mammals is preferably from 10 to 200 milligrams and dosage forms preferably contain from 2.5 to 100 milligrams.

Pharmaceutical compositions provided by the invention and useful for effecting tranquilization of mammals contain a compound of the formula I as active ingredient and one or more conventional pharmaceutically acceptable carriers, including such other conventional adjuvants as may be desired or necessary. Such compositions may be in conventional orally administerable forms such as tablets, capsules, granules, dispersible powders, elixirs, syrups, suspensions and the like or in conventional parenterally administerable forms such as an injectable sterile solution, suspension or the like, e.g., a sterile injectable aqueous suspension. Such compositions including applicable unit dosage forms thereof may be prepared according to any method known in the art for the manufacture of pharmaceutical compositions. The compositions of the invention adapted for oral or parenteral administration may contain from 1% to 90% by total weight of active ingredient in combination with the carrier, more usually 3% to 60%. The preferred unit dosage forms are the essentially solid forms adapted for oral administration.

A representative formulation for administering 3 to 4 times a day or as needed in treatment of anxiety and/or tension is a capsule prepared by conventional capsulating techniques and containing the following ingredients.

| Ingredient | Parts by Weight |
| --- | --- |
| 1-(p-chlorobenzyl)-7-chloro-2, 3-dihydro-imidazo[2,1-b]quinazolin-5(1H)-one | 10 |
| Lactose | 200 |

The generally preferred compounds of the formula I are those having one or more or all of the following features:

(a) $R^o$ being H; (b) R being halo, preferably chloro, or trifluoromethyl each located at position b of Ring A, particularly chloro; (c) $R_1$, $R_2$ and $R_3$ all being H;

(d) Z is

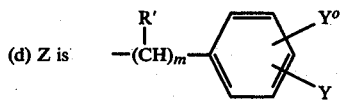

(e) m is 1; (f) R' is hydrogen or methyl; and (g) $Y^o$ is hydrogen and Y is hydrogen, fluoro or chloro.

In formula I when m is 2 or more it will be understood that the resulting R' groups may be, independently of each other, hydrogen or $C_1$-$C_2$ alkyl, but when m is greater than 1 it is generally preferred that no more than one of the resulting R' are other than hydrogen.

It will also be evident that Compounds I when R', $R_1$, $R_2$ and/or $R_3$ are other than hydrogen may exist in the form of diastereoisomers and such individual optional isomers may be separated and recovered by conventional techniques when found together in the reaction product.

The following Examples illustrate compounds of the invention and their preparation.

EXAMPLE 1

1-(o-chlorobenzyl)-7-chloro-2,3-dihydro-imidazo[2,1-b]quinazolin-5(1H)-one

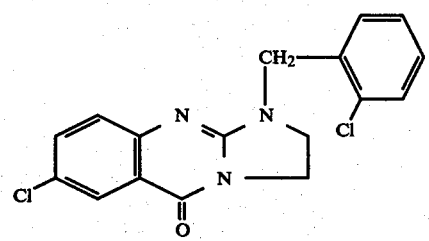

A solution of 1.0 g. of 3-(2-chloroethyl)-2,6-dichloro-3,4-dihydroquinazolin-4-one and 1.5 g. of 2-chlorobenzylamine in 50 ml. of ethanol and 1.0 ml of dimethylacetamide is stirred and heated at reflux for 12 hours. The solvent is removed by evaporation in vacuo and the residue dissolved in methylene chloride, washed with water, treated with charcoal, filtered and concentrated in vacuo to obtain a solid which is recrystallized from methylene chloride/pentane and filtered to obtain 1-(o-chlorobenzyl)-7-chloro-2,3-dihydro-imidazo[2,1-b]quinazolin-5(1H)-one, m.p. 173°–174° C.

EXAMPLE 2

Following the procedure of Example 1 the following compounds also representing the sub-classes of the invention in which n is 0 and m is 1 and conforming to the following formula IA as indicated in Table A, below, are prepared:

TABLE A

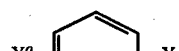

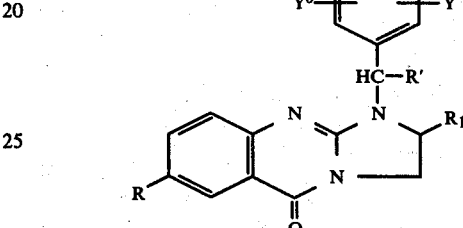

| Example | R | R' | Y | $Y^o$ | $R_1$ | m.p. |
| --- | --- | --- | --- | --- | --- | --- |
| 2A | chloro | H | H | H | H | 162–164° C. |
| 2B | chloro | H | H | H | —$CH_3$ | 143–145° C. |
| 2C | H | H | p-chloro | H | H | 119–121° C. |
| 2D | chloro | —$CH_3$ | H | H | H | 143–145° C. |
| 2E | chloro | H | p-chloro | H | H | 151–153° C. |
| 2F | chloro | —$CH_3$ | H | H | H | 144–145° C. |
| 2G | —$CF_3$ | H | o-chloro | H | H | 114–116° C. |
| 2H | —$CF_3$ | H | H | H | H | 145–147° C. |
| 2I | chloro | H | m-methyl | H | H | 144–146° C. |
| 2J | chloro | H | m-chloro | H | H | 170–172° C. |
| 2K | chloro | H | m-chloro | p-methyl | H | 138–141° C. |
| 2L | chloro | H | o-chloro | p-chloro | H | 188–190° C. |
| 2M | chloro | H | m-chloro | p-chloro | H | 206–208° C. |
| 2N | chloro | —$CH_3$ | p-chloro | H | H | 128–130° C. |

Notes:
Example 2D is (−)-isomer and Example 2F is (+)-isomer

The compound of Example 2B is also prepared by preparing the corresponding 1-unsubstituted compound (a compound of formula VI) by the procedure of Example 1 and then reacting said 1-unsubstituted compound first with sodium hydride and then with phenylmethyl bromide in DMA at about room temperature for 15 hours to obtain the compound of Example 2B on crystallization from ethanol.

EXAMPLE 3

Following the procedure of Example 1 the following compounds representing the sub-classes of the invention in which n is 0 and m is 0 and conforming to the following formula IB as indicated in Table B, below, are prepared:

TABLE B

IB

[Structure: compound of formula IB with substituents R, Y, Y°, R₁]

| Example | R | Y | Y° | R₁ | m.p. |
|---|---|---|---|---|---|
| 3A | chloro | p-fluoro | H | H | 226–227° C. |
| 3B | chloro | p-chloro | H | H | 222–223° C. |
| 3C | chloro | m-CF₃ | H | H | 175–177° C. |
| 3D | chloro | o-chloro | p-methyl | H | 145–147° C. |

EXAMPLE 4

Following the procedure of Example 1 the following 1,2,3,4-tetrahydro-6H-pyrimido[2,1-b]quinazolin-6-ones representing the sub-classes of the compounds of the invention in which n is 1 and m is 1 and having the following formula IC as indicated in Table C, blow, are prepared:

TABLE C

IC

[Structure: compound of formula IC]

| Example | R | R' | Y | Y° | R₁ | m.p. |
|---|---|---|---|---|---|---|
| 4A | chloro | H | H | H | H | 147–151° C. |
| 4B | chloro | H | p-chloro | H | H | 202–205° C. |
| 4C | chloro | H | p-fluoro | H | H | 166–168° C. |
| 4D | chloro | H | o-chloro | p-Cl | H | |
| 4E | chloro | H | m-chloro | p-Cl | H | |
| 4F | chloro | H | o-chloro | H | H | 193–195° C. |

EXAMPLE 5

Following the procedure of Example 1 the following compounds representing the sub-classes of the invention in which n is 1 and m is 0 and conforming to the following formula ID as indicated in Table D, below, are prepared:

TABLE D

ID

[Structure: compound of formula ID]

| Example | R | Y | Y° | m.p. |
|---|---|---|---|---|
| 5A | chloro | m-CF₃ | H | 185–187° C. |
| 5B | chloro | p-fluoro | H | 199–200° C. |

TABLE D-continued

ID

| Example | R | Y | Y° | m.p. |
|---|---|---|---|---|
| 5C | chloro | p-methyl | H | 172–173° C. |
| 5D | chloro | p-chloro | H | |

In the foregoing Examples the final products are recovered or purified by crystallization from methylene chloride or methylene chloride and pentane, except where noted.

EXAMPLE 6

Following the procedure of Example 1 the following additional compounds of the invention are prepared.

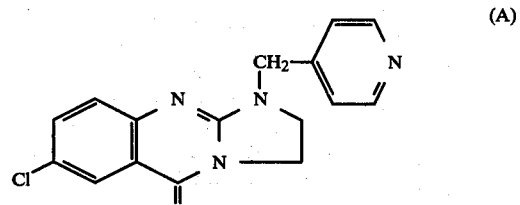

(A)

Solvent: isopropanol.
Crystallization from
Hexane/ether plus a few
drops of methanol,
m.p. 136–138° C.

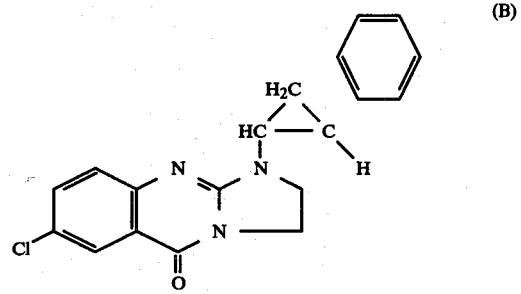

(B)

Solvent: isopropanol.
Crystallization from
Hexane/methylene chloride
plus a few drops of
ether, m.p. 136.5–138° C.

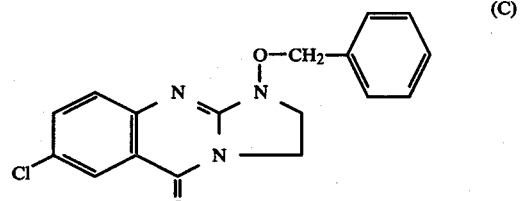

(C)

Solvent: isopropanol.
using benzylhydroxyamine
hydrochloride with triethylamine.
Crystallization from Hexane/ether,
m.p. 78–80° C.

(D) 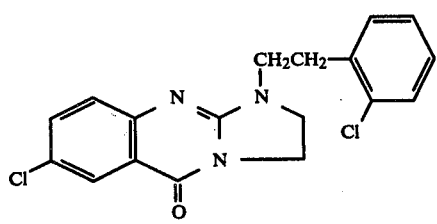
m.p. 116–118° C.

(E) 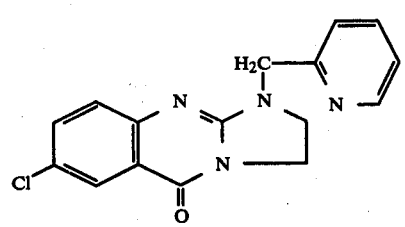
m.p. 170–173° C.

(F) 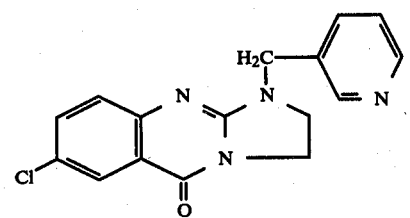
m.p. 153–155° C.

(G) 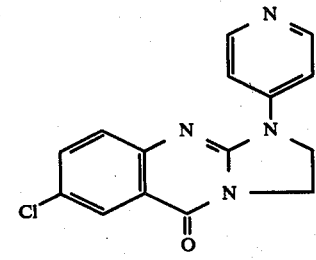
m.p. 151–154° C.

(H) 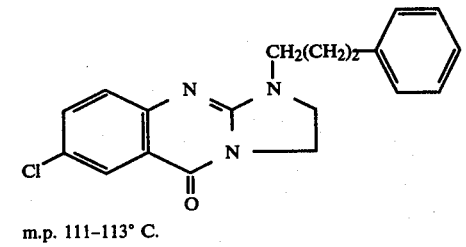
m.p. 111–113° C.

(I) 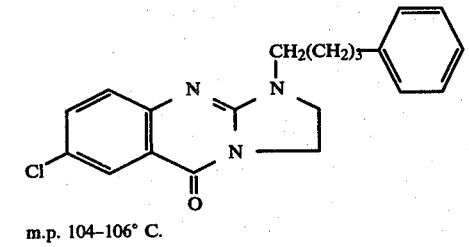
m.p. 104–106° C.

(J) 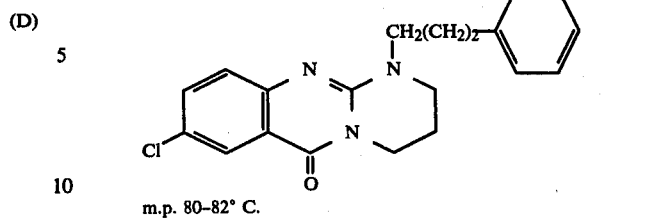
m.p. 80–82° C.

(K) 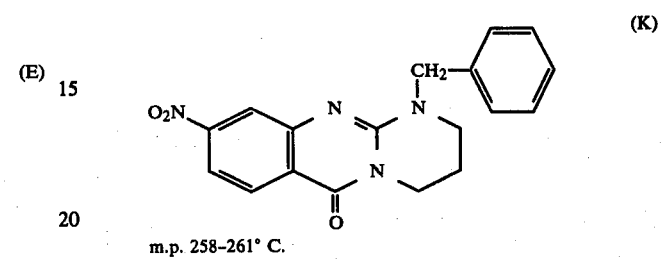
m.p. 258–261° C.

An evaluation of representative compounds of the invention in the Flunitrazepam Receptor Binding Assay gives the results in Table I, below. FBA Test No. 1 was employed where a single value is given whereas a range represents the results when both FBA Test No. 1 and FBA Test No. 2 were employed.

| Compound by Example | Response - % of Control |
|---|---|
| 1 | 2–3 |
| 2A | 1 |
| 2B | 5 |
| 2D | 15 |
| 2E | 5 |
| 3A | 8–18 |
| 4A | 1–2.6 |

What is claimed is:
1. The method of tranquilizing a mammal comprising administering to a mammal a tranquilizing effective amount of a compound of the formula:

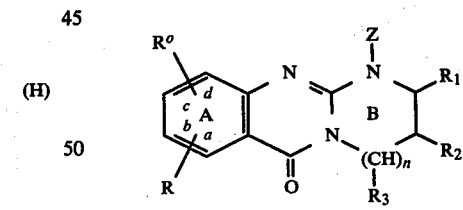

wherein
$R^o$ is hydrogen, halo of atomic weight of the 18 to 80, i.e. fluoro, chloro or bromo, or alkyl of 1 to 3 carbon atoms,
R is hydrogen, halo of atomic weight of from 18 to 80, alkyl of 1 to 4 carbon atoms, nitro or trifluoromethyl,
n is 0 or 1,
$R_1$, $R_2$ and $R_3$ are each independently hydrogen or alkyl of 1 or 2 carbon atoms, with the proviso that no more than 2 of $R_1$, $R_2$ and $R_3$ are other than hydrogen,
Z is (a) 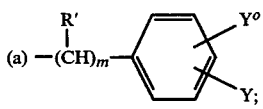

(b) 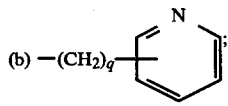

(c) 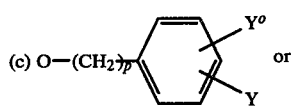 or (d) 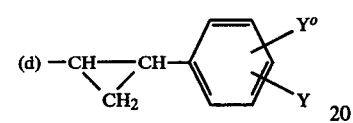

R' is hydrogen or alkyl of 1 or 2 carbon atoms,
$Y^o$ is hydrogen, halo of atomic weight of from 18 to 80 or alkyl of 1 to 3 carbon atoms,
Y is hydrogen, halo of atomic weight of from 18 to 80, alkyl of 1 to 4 carbon atoms, trifluoromethyl or nitro,
p is 1 or 2,
q is 0, 1 or 2, and
m is 0, 1, 2, 3 or 4.

2. The method of claim 1 in which $R_1$, $R_2$ and $R_3$ are each H.

3. The method of claim 2 in which $R^o$ is H.

4. The method of claim 1 in which R is halo or trifluoromethyl in the b position of Ring A.

5. The method of claim 3 in which R is chloro or trifluoromethyl in the b position of Ring A.

6. The method of claim 1 in which the compound is 1-(o-chlorobenzyl)-7-chloro-2,3-dihydro-imidazo[2,1-b]quinazolin-5(1H)-one.

7. The method of claim 1 in which the compound is 1-benzyl-7-chloro-2,3-dihydro-imidazo[2,1-b]quinazolin-5(1H)-one.

8. The method of claim 1 in which the compound is 1-benzyl-8-chloro-1,2,3,4-tetrahydro-6H-pyrimido[2,1-b]quinazolin-6-one.

9. The method of claim 1 in which the compound is 1-(p-chlorobenzyl)-7-chloro-2,3-dihydro-imidazo[2,1-b]quinazolin-5(1H)-one.

10. The method of claim 1 in which the compound is 1-(p-fluorobenzyl)-8-chloro-1,2,3,4-tetrahydro-6H-pyrimido[2,1-b]quinazolin-6-one.

11. A compound of the formula

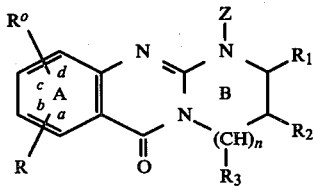

I wherein
$R^o$ is hydrogen, halo of atomic weight of from 18 to 80, i.e. fluoro, chloro or bromo, or alkyl of 1 to 3 carbon atoms,
R is hydrogen, halo of atomic weight of from 18 to 80, alkyl of 1 to 4 carbon atoms, nitro or trifluoromethyl,
n is 0 or 1,
$R_1$, $R_2$ and $R_3$ are each independently hydrogen or alkyl of 1 or 2 carbon atoms, with the proviso that no more than 2 of $R_1$, $R_2$ and $R_3$ are other than hydrogen,
Z is (a) 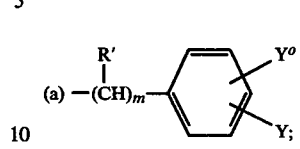

(b) 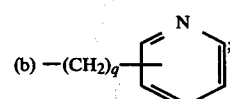

(c) 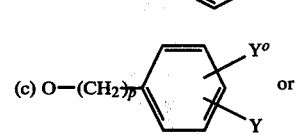 or (d) 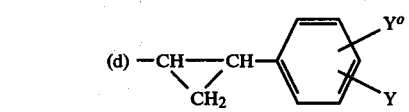

R' is hydrogen or alkyl of 1 or 2 carbon atoms,
$Y^o$ is hydrogen, halo of atomic weight of from 18 to 80 or alkyl of 1 to 3 carbon atoms,
Y is hydrogen, halo of atomic weight of from 18 to 80, alkyl of 1 to 4 carbon atoms, trifluoromethyl or nitro,
p is 1 or 2,
q is 0, 1 or 2, and
m is 0, 1, 2, 3 or 4,
with the proviso that R is other than hydrogen when n is 0 and Z is of type (a).

12. A compound of claim 11 in which $R_1$, $R_2$ and $R_3$ are each H.

13. A compound of claim 12 in which $R^o$ is H.

14. A compound of claim 11 in which R is halo or trifluoromethyl in the b position of Ring A.

15. A compound of claim 13 in which R is chloro or trifluoromethyl in the b position of Ring A.

16. The compound of claim 11 which is 1-(o-chlorobenzyl)-7-chloro-2,3-dihydro-imidazo[2,1-b]quinazolin-5(1H)-one.

17. The compound of claim 11 which is 1-benzyl-7-chloro-2,3-dihydro-imidazo[2,1-b]quinazolin-5(1H)-one.

18. The compound of claim 11 which is 1-benzyl-8-chloro-1,2,3,4-tetrahydro-6H-pyrimido[2,1-b]quinazolin-6-one.

19. The compound of claim 11 which is 1-(p-chlorobenzyl)-7-chloro-2,3-dihydro-imidazo[2,1-p]quinazolin-5(1H)-one.

20. The compound of claim 11 which is 1-(p-fluorobenzyl)-8-chloro-1,2,3,4-tetrahydro-6H-pyrimido[2,1-b]quinazolin-6-one.

21. A compound of claim 1, 14 or 15 in which Z is

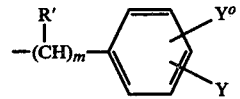

in which m is 1, R' is hydrogen or methyl, $Y^o$ is hydrogen and Y is hydrogen, fluoro or chloro.

22. A pharmaceutical composition comprising an inert pharmaceutically acceptable carrier and a tranquilizing effective amount of a compound of claim 11.

* * * * *